(12) United States Patent
Heinz et al.

(10) Patent No.: US 8,231,585 B2
(45) Date of Patent: *Jul. 31, 2012

(54) MEMBRANE SYRINGE

(75) Inventors: Jochen Heinz, Flintbek (DE); Dieter Schilling, Aukrug-Innien (DE)

(73) Assignee: Transcoject GmbH, Neumuenster (DE)

( * ) Notice: Subject to any disclaimer, the term of this patent is extended or adjusted under 35 U.S.C. 154(b) by 712 days.

This patent is subject to a terminal disclaimer.

(21) Appl. No.: 12/034,865

(22) Filed: Feb. 21, 2008

(65) Prior Publication Data

US 2008/0140016 A1    Jun. 12, 2008

Related U.S. Application Data

(63) Continuation of application No. 10/684,889, filed on Oct. 14, 2003, now Pat. No. 7,367,964.

(30) Foreign Application Priority Data

Oct. 15, 2002  (DE) ................................. 102 47 963

(51) Int. Cl.
*A61M 5/31* (2006.01)
*A61M 5/00* (2006.01)
(52) U.S. Cl. .................... 604/263; 604/243; 604/111
(58) Field of Classification Search .................. 604/110, 604/111, 263, 200, 187, 192, 240–243, 195
See application file for complete search history.

(56) References Cited

U.S. PATENT DOCUMENTS

| 3,989,044 | A | * | 11/1976 | Meierhoefer | 604/192 |
| 6,068,614 | A | * | 5/2000 | Kimber et al. | 604/200 |
| 6,126,640 | A | * | 10/2000 | Tucker et al. | 604/187 |
| 6,173,852 | B1 | * | 1/2001 | Browne | 215/247 |
| 7,367,964 | B2 | * | 5/2008 | Heinz et al. | 604/263 |

* cited by examiner

*Primary Examiner* — Matthew F Desanto
(74) *Attorney, Agent, or Firm* — McGlew and Tuttle, P.C.

(57) ABSTRACT

The syringe is a prefillable or prefilled syringe having a syringe cylinder which is delimited to one side by a plunger and which to the other side opens into a syringe connection having a free end closed by a membrane. The syringe cylinder, the syringe connection and the closing membrane are formed as one piece as a plastic injection molded part.

20 Claims, 5 Drawing Sheets

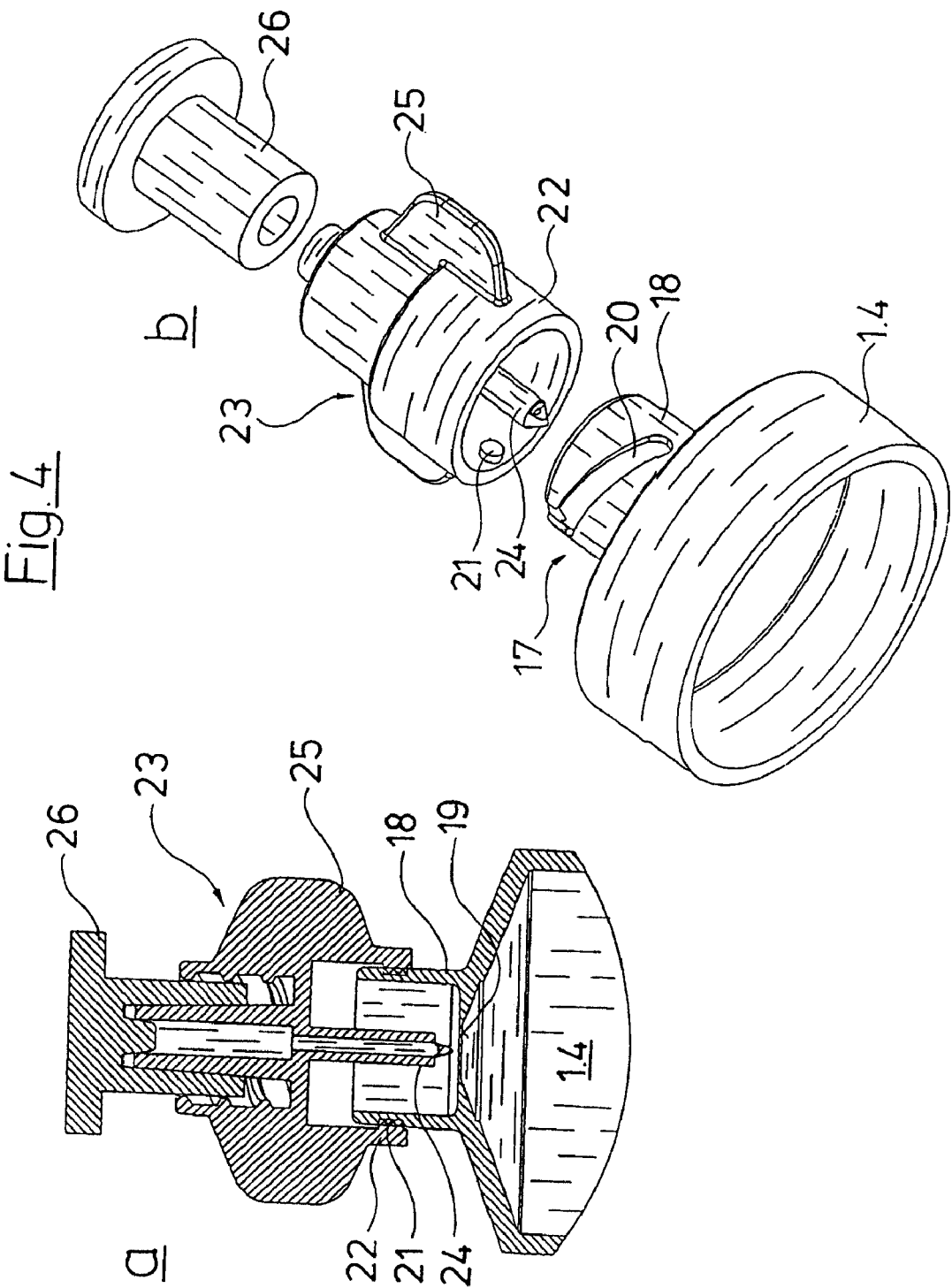

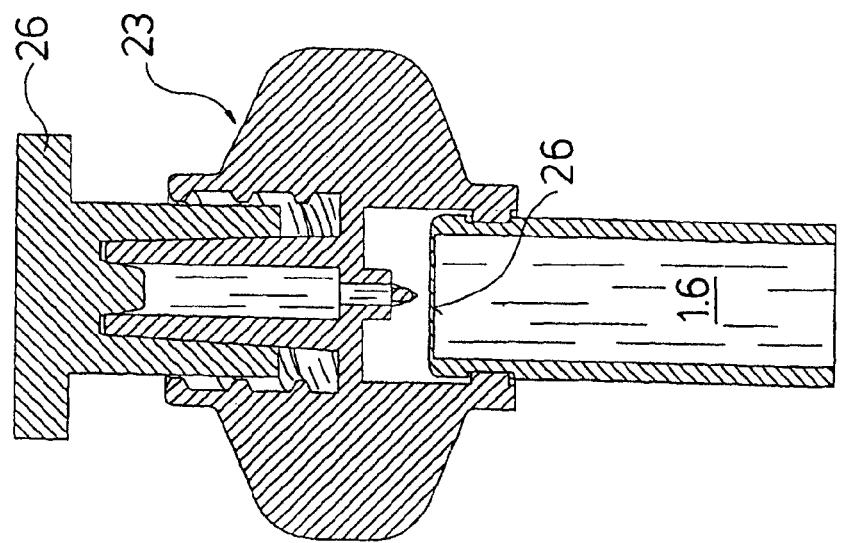
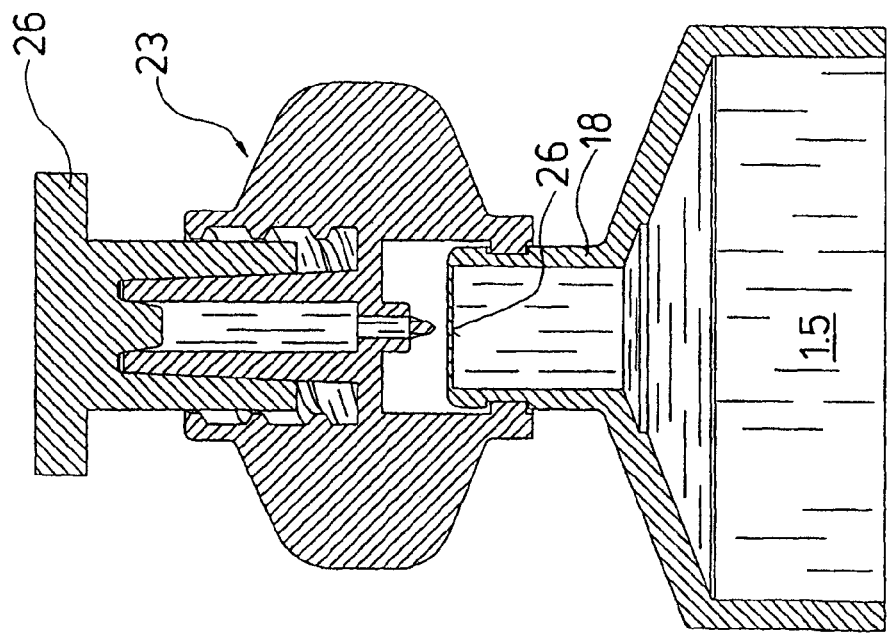

MEMBRANE SYRINGE

CROSS REFERENCE TO RELATED APPLICATIONS

This application is a continuation under 37 CFR 1.53(b) of pending prior application Ser. No. 10/684,889 filed on Oct. 14, 2003 now U.S. Pat. No. 7,367,964 and claims the benefit of priority under 35 U.S.C. §119 of German Application DE 102 47 963.1 filed Oct. 15, 2002, the entire contents of which are incorporated herein by reference.

FIELD OF THE INVENTION

The present invention relates to a syringe, in particular to a prefillable or prefilled syringe, having a syringe cylinder with an end provided with a syringe connection having a free end.

BACKGROUND OF THE INVENTION

Prefilled syringes of this type are known; they are usually manufactured with a syringe cylinder of glass, wherein on that side of the syringe cylinder distant to the syringe plunger there is provided a syringe connection which is sealingly closed by way of a further component.

With the state of the art known from U.S. Pat. No. 5,989,227, this further component is a sealing element which is rigidly connected to and is to remain on the syringe connection. For removing the fluid located in the syringe cylinder this closure must be pierced by way of a cannula. The solution known from U.S. Pat. No. 5,135,496 is more favorable inasmuch as this further component already has a though-bore which at the end is sealed by way of a closure plug which must first be directly removed before use. The embodiment form described here however is extremely complicated in its construction since apart from the syringe cylinder three or four further components are required.

U.S. Pat. No. 5,833,653 discloses a syringe connection which is closed by way of a further component which although comprising a central though-bore, is however closed by way of a membrane. In order to release this connection the syringe cylinder is pressed in, by which means the membrane is deflected outwards due to the increased inner pressure, and here is pierced by a spike-like plug which projects into the Luer connection of the syringe. Disregarding the fact that this solution is also complicated in its design due to the multitude of components, the design of the membrane is very difficult with regard to manufacturing technology and is thus expensive. Specifically it needs to be thin enough such that with the impingement of pressure it bulges sufficiently towards the spike, and on the other hand it must be thick enough to reliably close off the contents.

For syringes with a syringe cylinder consisting of plastic, a similar closure variant is known from U.S. Pat. No. 5,624,402. The closure element to be placed onto the syringe connection likewise consists of a multitude of components and requires a costly manufacture and is thus expensive.

SUMMARY OF THE INVENTION

Against this background it is the object of the invention to create a syringe according to the known type, which is inexpensive and may be easily manufactured, but which at the same time however ensures a sealed closure of the fluid located therein.

The basic concept of the present invention is to design the syringe cylinder together with the syringe connection and the membrane closing this as one piece as a plastic injection molded part. By way of this the multitude of parts which is otherwise common is minimized, by which means the manufacturing costs may be reduced to a minimum, in particular with the large batch numbers produced here. At the same time the design according to the invention also offers a large safety with regard to sealing, since with the selection of a suitable, diffusion-tight plastic only the region between the plunger and the syringe cylinder remains to be sealed. This region must be sealed with all syringe designs and this has been technically mastered and may be realized with relatively little cost with regard to manufacturing technology. A further advantage of the membrane closure manufactured of one piece with the syringe is that the content, which is typically a medicine, only comes into contact with one and the same plastic. Furthermore it is also advantageous that the syringe is completely tight also with all subsequent processing steps such as autoclaving, labeling etc. and is not compromised by way of these steps. The sealing can be checked visually so that the sterility is considerably simpler to verify than is the case with the state of the art.

A syringe connection within the context of the invention is to be understood as the connection provided at the that end of the syringe which is distant to the plunger, which is either a Luer connection or a Luer lock connection, but also a special connection onto which then a component is placed which forms the actual cannula or other closure.

The syringe according to the invention, at the free end of the syringe connection is preferably provided with a cap which comprises a spike for piercing the membrane. At the same time it is particularly favorable if the cap is designed such that it at least engages over the free end of the syringe connection in order to protect the whole syringe connection from germs and simultaneously to form a tool with which the membrane may be pierced in a directed manner, and thus the syringe may be opened for the directed application.

It is particularly advantageous if the cap and the syringe are matched to one another such that the cap is arranged in a first position in which the spike lies opposite the membrane and arranged at a distance to this. In this position the cap merely serves for protecting the syringe connection. From this position the cap may be brought into a second position in which the spike penetrates through the membrane. In this manner the membrane may be pierced, i.e. the syringe may be opened for its directed use without having to remove the cap from the syringe, by which means the danger of contamination with germs is reduced further since the spike which after opening the usually sterile package likewise lies sterile in the inside of the cap, then without further removal may be introduced directly into the membrane. Only afterwards is the cap removed as the case may be, in order to connect the syringe.

The invention however envisages design variants which will be described further below and with which the cap after piercing the membrane, is not to be removed but simultaneously forms a connection component. Such a component may for example be formed by a tubular spike which opens into the inside of a Luer connection or Luer lock connection provided on the outer side of the cap. With such a design the cap usefully at its cannula-side end is yet provided with a (further) protective cap which engages over at least the Luer connection and closes this to the outside. With the application of a Luer lock connection on the outer side this may either be completely engaged over by the protective cap or however in a manner such that the Luer connection which is always formed within the Luer lock connection is engaged over.

If the cap as is envisaged in a further formation of the invention is formed as a further component not only for opening the membrane, but also for leading through the fluid located in the syringe, then this cap may usefully be connected to the syringe cylinder by way of a bayonet, wherein the bayonet is designed such that the cap engages over the syringe connection, and the actual bayonet path has a gradient in a manner such that with the transfer from the first into the second position the cap is moved axially in the direction of the syringe cylinder. This bayonet path with a gradient then at the same time forms the path guide for a targeted penetration of the spike into the membrane, wherein here one may create a relatively high pressure with a relatively small force of the hand, depending on the gradient. This permits a relatively thick design of the membrane which in turn is favorable with regard to manufacturing technology.

Instead of the previously mentioned intermediate component, thus a cap with a through-flow function, the syringe connection according to the invention may also be directly formed as a Luer connection or preferably as a Luer lock connection, wherein the membrane preferably only closes the Luer connection so that the thread present in the Luer lock connection may be used for fastening and for a guide path.

In order to prevent the cap from being unintentionally brought from the first into the second position, it is useful to provide locking means between the cap and the syringe connection or syringe cylinder, which ensures that one needs to overcome a predefined force for conveying from the first into the second position. Such locking means for example may be formed by a ring tapering conically towards the tip on the outer circumference of the Luer lock connection, or corresponding ring sections which engage into a corresponding groove or groove section on the inner circumference of the cap. The cap is preferably formed divided in this region so that the remaining circumferential parts may spring outwards in order to overcome this ring. Such a conically tapering ring on the outer circumference of the Luer lock connection furthermore has the advantage that not only cannula but where appropriate a flexible tubing may be directly connected to this syringe closure in that this tubing is pushed over the ring. The conicity of the ring not only encourages the sliding on of the flexible tuning, but also at its outer circumference provides for an increased sealing effect which as a rule is sufficient for a reliable sealing between the flexible tubing and the syringe body.

The syringe, in particular the syringe cylinder with the membrane which are formed as one piece at the same time are advantageously manufactured of polyolefins, preferably of polypropylene (PP) or cyclo-olefin polymers (COP) or other barrier plastics.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

BRIEF DESCRIPTION OF THE DRAWINGS

In the drawings:

FIG. 2a the cannula-side end of a syringe cylinder of a syringe according to the invention with a placed-on cap, in a first position and in a longitudinal section;

FIG. 2b the cap in a longitudinal section;

FIG. 2c the cannula-side end of the syringe cylinder in a longitudinal section;

FIG. 2d the cannula-side end of the syringe cylinder with a placed-on cap in the second position, in a longitudinal section;

FIG. 2e is a lateral view of the embodiment shown in FIG. 2a;

FIG. 3a is a longitudinal section of the cap and the cannula-side end of the syringe cylinder in the first position;

FIG. 3b is a longitudinal section of the cap;

FIG. 3c is a longitudinal section of the cannula-side end of the syringe cylinder;

FIG. 3d the cannula-side end of the syringe cylinder with a cap in the second position, in a longitudinal section;

FIG. 3e is a lateral view of the cap;

FIG. 3f is a lateral view of the cannula-side end of the syringe cylinder;

FIG. 3g is a lateral view of the two components in a first position;

FIG. 4 is a fourth embodiment variant with an intermediate component, and specifically;

FIG. 4a is a longitudinal section of one variant of the cannula-side end of the syringe cylinder with a placed-on intermediate component in a first position, with a protective cap;

FIG. 4b is an exploded view of the previously mentioned components;

FIG. 5 is a longitudinal section of one variant of the cannula-side end of the syringe cylinder with a placed-on intermediate component, in a first position, with a protective cap; and FIG. 6 is a longitudinal section of a further variant of the cannula-side end of the syringe cylinder with a placed-on intermediate component in a first position with a protective cap.

DESCRIPTION OF THE PREFERRED EMBODIMENT

Figure 1:
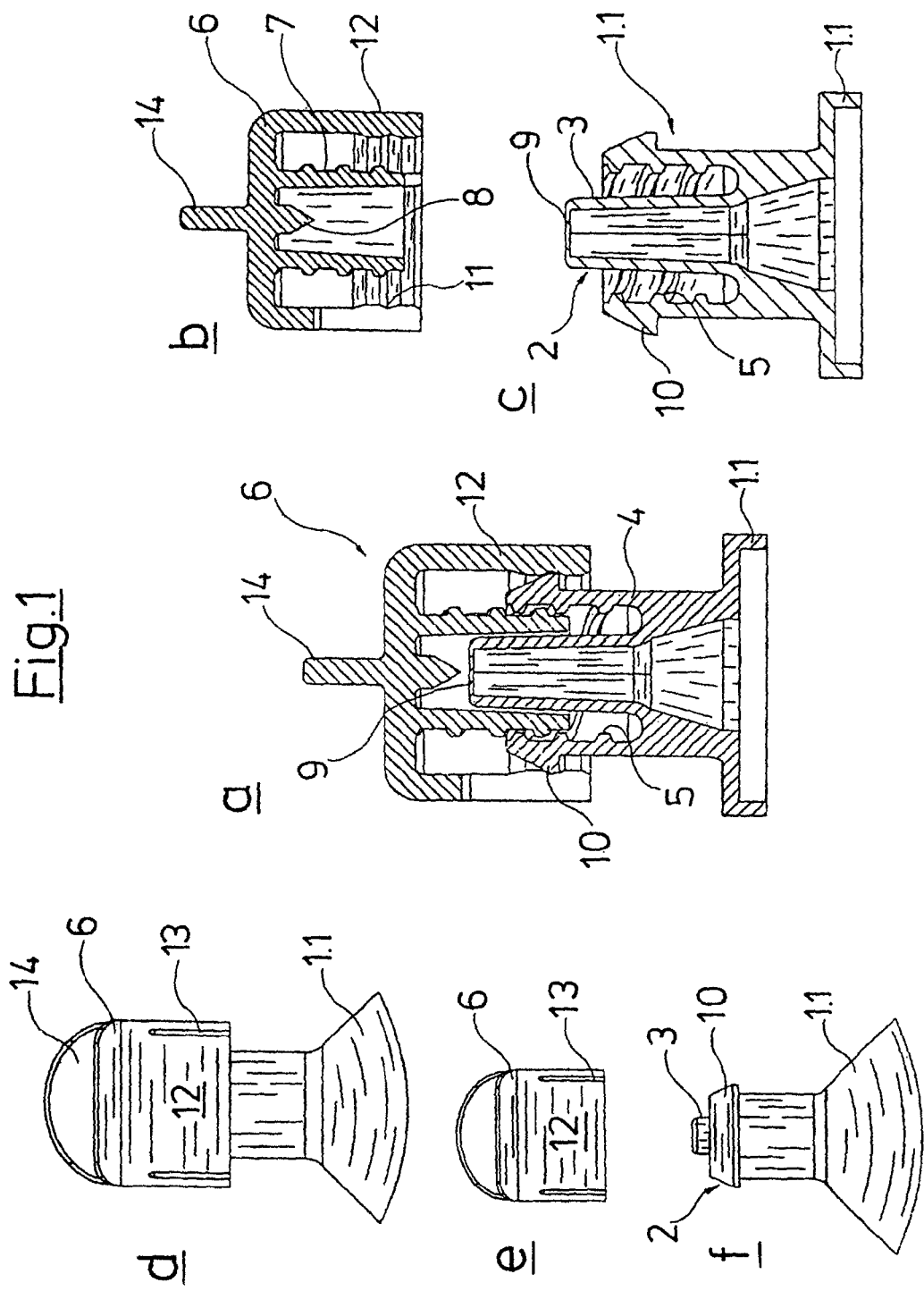
FIG. 1a is a longitudinal section of the cannula-side end of a syringe cylinder of a syringe according to the invention with a placed-on cap, in a first position.
FIG. 1b is a longitudinal section of the cap.
FIG. 1c is a longitudinal section of the cannula-side end of the syringe cylinder.
FIG. 1d is a side view of the cannula-side end of the syringe cylinder with a placed-on cap.
FIG. 1e is a side view of the cap.
FIG. 1f is a side view of the cannula-side end of the syringe cylinder.

Referring to the drawings in particular FIG. 1 shows a Luer lock connection 2 integrally formed onto the cannula-side end of the syringe cylinder which is not shown in detail. The Luer lock connection 2 in the known manner consists of a Luer connection 3 which at a distance is surrounded by a cylindrical wall section 4 on whose inner side there is provided a thread 5.

For protecting the syringe connection formed by the Luer lock connection 2 there is provided a cap 6 which is formed essentially cup-shaped and comprises an inner cylinder 7 which carries an outer thread which may be brought to engage with the thread 5 of the Luer lock connection 2. Within the inner cylinder 7 there is provided a spike 8 which in a first position according to FIG. 1a is arranged at a small distance to a membrane 9 which closes the Luer connection 3 and seals it to the top. As is clearly evident from FIGS. 1a and 1c the syringe cylinder, Luer lock connection 2 as well as the membrane 9 are formed as one piece and specifically as an injection molded plastic part.

So that the cap 6 remains in its first position shown in FIG. 1a in which the spike 8 is arranged at a distance to the membrane 9, there are provided locking means, and specifically in the form of a ring 10 which tapers conically towards the tip and which is integrally formed on the outer circumference of an outer cylinder 12 of the cap 6. The outer cylinder 12 which is arranged at a distance to the inner cylinder 7 and is arranged surrounding this as well as the end-side part of the wall section 4, has in total four longitudinal recesses 13 distributed over the circumference, so that the outer cylinder sections formed by way of this, for placing on the cap 6 into the first position shown in FIG. 1a, may overcome the ring 10 until this ring lies in the groove 11. In this position, as FIG. 1a clearly shows, the inner cylinder 7 is immersed up to roughly half into the thread 5 of the Luer lock connection 2, so that on the one hand there is provided a stable seating as well as a mechanical protection of the Luer lock connection, and on the other hand there still remains a free path in order to bring the cap 6 into a second position in which after overcoming the locking means 10, 11 the spike 8 is completely immersed into the membrane 9 and thus in order to open the lumen of the Luer connection 3. A grip piece 14 is provided on the upper side of the cap in order to bring the cap 6 into this position.

The syringe according to the invention is prefilled at the factory and at the end distant to the cannula is provided with a plunger in a manner known per se. The cannula end 1.1 is provided with the cap 6, and specifically in the first position as is shown in FIG. 1a. The syringe which is thus completed is packed in a sterile manner. For use firstly the sterile package is opened for the first time, whereupon the user grips the cap 6 at the grip piece 14 and from this first position screws it in whilst completely overcoming the locking force, i.e. up to the abutment, into the thread 5 of the Luer lock connection 2. At the same time the thread 5 serves for guiding as well as force transmission. The spike 8 at the same time works its way into the membrane 9 and opens the lumen of the Luer connection 3. By rotating in the opposite direction the cap is then removed and a cannula preferably with a Luer lock connection is fastened in a manner known per se. Alternatively via the wall section 4 one may also directly connect a flexible tubing, with this then the ring 11 tapering conically towards the tip serves as a guide as well as a sealing ring.

Figure 2:
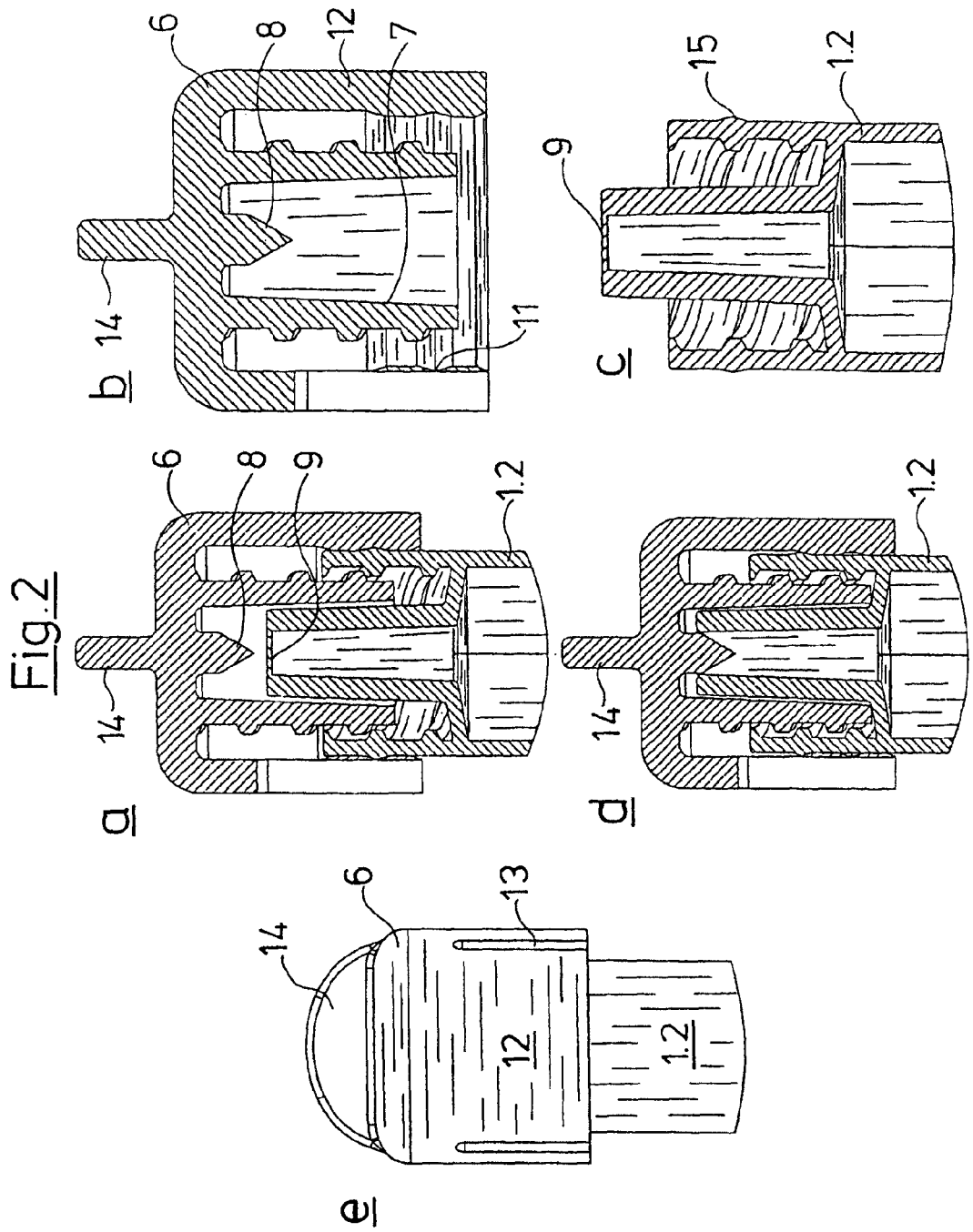
FIG. 2 an alternative embodiment, and specifically

The embodiment variant according to FIG. 2 differs from that previously described in that here there is provided no conically tapering ring 10, but instead of this a locking projection 15 is formed on the outer side of the wall section 4, and this projection lockingly cooperates with the groove 11 in the same manner as with the embodiment variant according to FIG. 1. In FIG. 2 there are shown the first position in which the spike 8 is arranged lying opposite the membrane at a distance, in the representation according to FIG. 2a, and the second position in which the spike 8 has completely penetrated through membrane 9 and has penetrated into the Luer connection 3 at the end face. At the same time the end-face free end of the inner cylinder 7 bears on the abutment, specifically on the base of the Luer lock connection 2.

The cannula end 1.2 of the syringe is shown somewhat differently than in FIG. 1, in order by way of example to emphasize that here it may be the case of a cannula end of any syringe.

Figure 3:
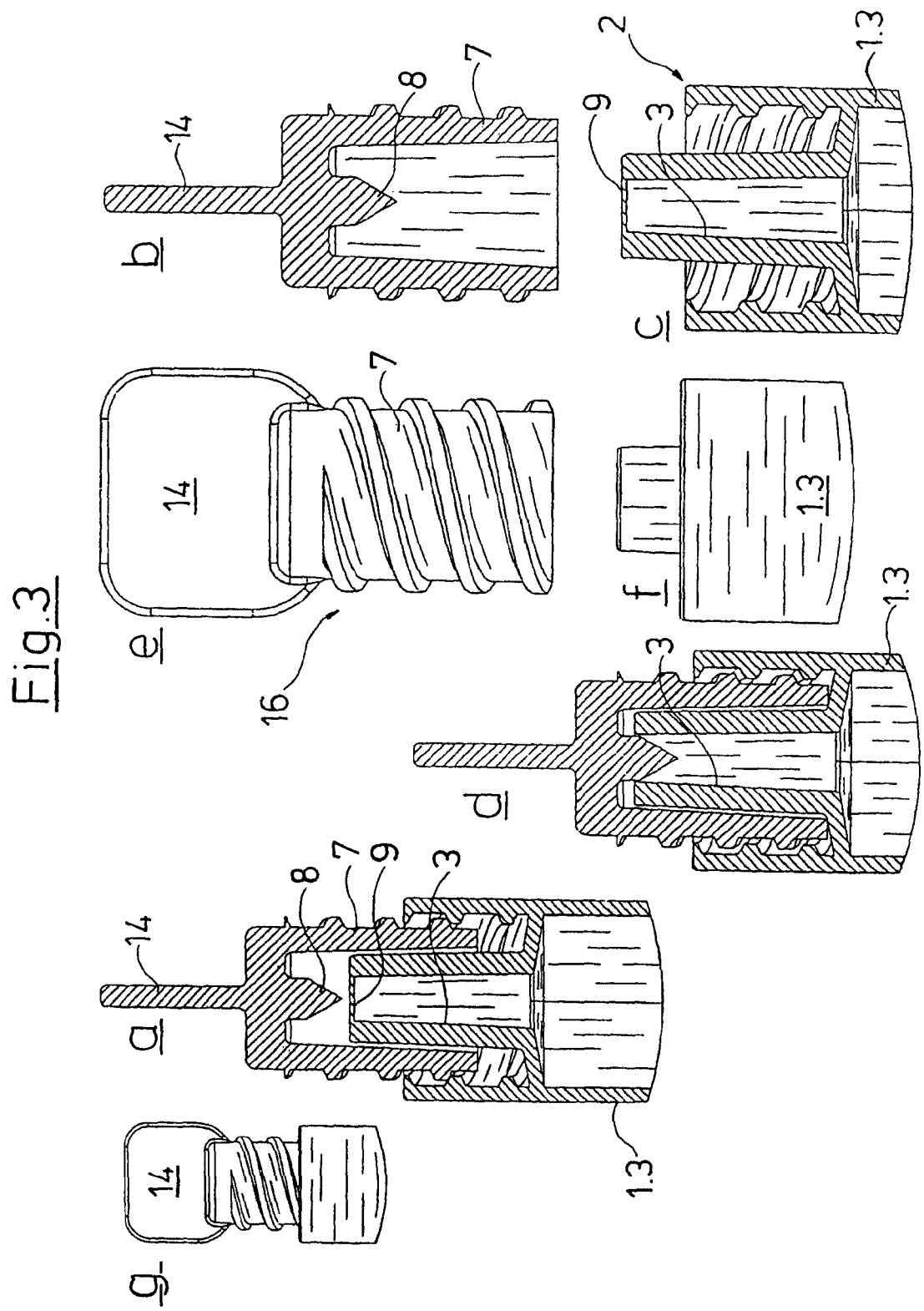
FIG. 3 a third embodiment variant and specifically.

By way of FIG. 3 there is shown a third embodiment variant which differs from that previously described by way of FIG. 2 essentially at the cap side. Specifically there is provided a cap 16 here which consists of the inner cylinder 7, the spike 8 as well as the grip piece 14 and a corresponding end-face connection wall. Since here the cap 16 merely engages over the Luer connection 3 and no outer cylinder is provided, the locking means here are also done away with. On the outer circumference of the wall section 4 there is neither provided a locking projection nor a ring. Irrespective of this the cannula ends 1.1 and 1.2 described previously by way of FIGS. 1 and 2 respectively may be used with the simplified cap 16 according to FIG. 3.

With the embodiment form according to FIG. 4 the cannula end 1.4 of the syringe cylinder opens into a syringe connection 17 which in contrast to the previously described embodiment forms is not formed by a Luer lock connection but by a cylinder connection 18 which at its end proximal to the syringe cylinder comprises a membrane 19. On the outer side of the cylinder section 18 there are integrally formed two grooves 20 displaced by 180° to one another with a thread-like gradient. Guide studs 21 engage into these grooves 20 and these studs are displaced to one another likewise by 180° on the inner circumference of the cylinder section 22 which forms part of an intermediate component 23 which on the cannula-side is provided with a Luer lock connection 2. The Luer lock connection 2 is connected by an end-face wall to the cylinder section 22 on which a hollow spike 24 is integrally formed, whose inner channel is connected to the lumen of the Luer connection 3 of the Luer lock connection 2. On the outer side of the intermediate component 23 there are provided two grip pieces likewise displaced by 180° which serve the handling of the component and whose shape and arrangement are to be deduced in detail from FIG. 4.

A protective cap 26 which is pushed on as is evident from FIG. 4a protects the Luer connection 3. This protective cap with a blunt spike engages into the lumen of the Luer connection 3.

The prefilled syringe is supplied as is shown in FIG. 4a, i.e. the intermediate component 23 is located in a first (upper) position of the grooves 20. The guide bolts 21 thus already lie in the grooves 20 so that the cylinder section 22 with its inner circumference is led on the outer circumference of the cylinder section 18. The protective cap 26 covers the Luer connection 3 of the Luer lock connection 2. For opening the membrane 19 the intermediate component 23 is gripped by way of the grip pieces and rotated along the grooves 20 into the second position. By way of the fact that the grooves 20 run obliquely from the top to the bottom (with respect to FIG. 4), then by rotating the intermediate component 23 this is lowered with respect to the cannula end or approaches this end. At the same time the hollow spike 24 pierces the membrane 19 and thus creates a fluid-leading connection between the inside of the syringe cylinder and the lumen of the Luer connection 3. Then only the protective cap 26 is to be removed, whereupon a cannula may be attached and the syringe may be used in its directed manner.

Two further embodiment variants of the invention are yet shown by way of FIGS. 5 and 6, and specifically with regard to the cannula end of the syringe cylinder 1.5 and 1.6 respectively. The intermediate component 23 as well as the protective cap 26 with this are identical (disregarding the length of the hollow spike) to the designs described by way of FIGS. 4a and 4b.

In contrast to the cannula end of the syringe cylinder 1.4, with the syringe cylinder 1.5 the membrane 27 is not arranged at the base of the cylinder section 18, but at the upper end of this. This has the advantage that a smooth ending without rear projecting parts arises which is easily handled. Furthermore the possible filling volume of the syringe cylinder is increased and the length of the hollow spike 24 is shortened. This also applies to the embodiment variant represented by way of FIG. 6 with which the cannula end of the syringe cylinder 1.6 merges into the syringe cylinder in a flush manner. This variant is to particularly emphasize the fact that the invention may be applied with syringe cylinder of almost any shape.

The previously described embodiment examples are only to be understood as examples and are not limiting. The previously described features may also be applied individually or in a varying combination. In a simplified embodiment e.g. a Luer connection provided with a membrane may also be provided which may be opened by way of a cap able to be placed on, or other suitable tool.

While specific embodiments of the invention have been shown and described in detail to illustrate the application of the principles of the invention, it will be understood that the invention may be embodied otherwise without departing from such principles.

What is claimed is:

1. A syringe comprising:
   a syringe cylinder having an end, said syringe cylinder comprising a cylinder portion and a lock connection portion, said cylinder portion being integrally connected to said lock connection portion;
   a syringe connection provided on said end of said syringe cylinder, said syringe connection comprising a Luer connection element, said Luer connection element comprising an internal thread;
   a cap having a puncture element, said cap being movably mounted when attached to said syringe connection such that said cap is movable from a first position to a second position, said cap having a cap portion, said cap portion engaging said lock connection portion, said syringe connection being arranged on one side of said cap; and
   a membrane integrally connected to said syringe connection to form a one-piece sealed syringe connection structure, said puncture element being located at a spaced location from said membrane with said cap in said first position, said puncture element penetrating said membrane in said second position.

2. A syringe in accordance with claim 1, wherein said cap defines an interior cap space, said syringe connection being located within said interior cap space.

3. A syringe in accordance with claim 2, wherein said cap has an inner surface, said inner surface defining said interior cap space, said Luer connection element being located opposite said inner surface.

4. A syringe in accordance with claim 3, wherein said inner surface defines said puncture element of said cap.

5. A syringe in accordance with claim 4, wherein said puncture element is arranged directly opposite said membrane in a first position.

6. A syringe in accordance with claim 4, wherein said syringe connection comprises an outer cylindrical wall and an inner cylindrical wall, said outer cylindrical wall being integrally connected to said inner cylindrical wall, said outer cylindrical wall and said inner cylindrical wall defining a recess, said cap having an inner cylindrical wall, said inner cylindrical wall comprising said inner surface, at least a portion of said inner cylindrical wall being arranged in said recess.

7. A syringe in accordance with claim 1, further comprising a means for retaining said cap in a first position such that force is required to move said cap from said first position to a second position, said puncture element of said cap being at a spaced location from said syringe connection when said cap is in said first position.

8. A syringe in accordance with claim 7, wherein said puncture element punctures said membrane when said cap is in said second position.

9. A syringe in accordance with claim 1, wherein said syringe connection has an inner surface, said inner surface defining said internal thread.

10. A syringe in accordance with claim 1, wherein said syringe cylinder is integrally connected to said syringe connection.

11. A syringe cylinder comprising:
    a membrane;
    a syringe connection piece in the form of a Luer connection, said Luer connection having an inner cylindrical wall and an outer wall, said outer wall and said inner cylindrical wall defining a space, open at one end, for receiving a portion of a cap, said inner cylindrical wall being integrally connected to said membrane to form a unitary syringe cylinder structure, said syringe cylinder structure having a lumen defined by said membrane and said inner cylindrical wall, said syringe cylinder structure being formed as a one-piece plastic injection molded part, wherein said membrane is not punctured when said cap is attached to said syringe connection piece.

12. A syringe cylinder in accordance with claim 11, wherein said syringe cylinder structure consists of polyolefins.

13. A syringe cylinder in accordance with claim 12, wherein said polyolefins comprise at least one of polypropylene and cyclo-olefin polymers.

14. A syringe cylinder in accordance with claim 11, wherein said syringe connection piece has a lock connection having an internal thread, said lock connection including a ring, said ring tapering conically toward a free end of said syringe connection piece.

15. A syringe cylinder in accordance with claim 11, wherein said outer wall defines internal threads for receiving external threads of the cap.

16. A syringe cylinder comprising:
    a membrane;
    a syringe connection piece in the form of a Luer connection, said Luer connection having an inner cylindrical wall and an outer wall, said outer wall and said inner cylindrical wall defining a space for receiving a portion of a cap, said inner cylindrical wall being integrally connected to said membrane to form a unitary syringe cylinder structure, said syringe cylinder structure having a lumen defined by said membrane and said inner cylindrical wall, said syringe cylinder structure being formed as a one-piece plastic injection molded part;
    a retaining element for retaining a cap in a first position such that a force is required to move the cap from the first position to a second position, wherein at least a portion of said cap punctures said membrane in said second position, said at least said portion of said cap being at a spaced location from said membrane when said cap is attached to said syringe connection in said first position.

17. A syringe cylinder in accordance with claim 16, wherein said syringe cylinder structure consists of polyolefins.

18. A syringe cylinder in accordance with claim 17, wherein said polyolefins comprise at least one of polypropylene and cyclo-olefin polymers.

19. A syringe cylinder in accordance with claim 16, wherein said retaining element includes a lock connection having an internal thread, said lock connection including a ring, said ring tapering conically toward a free end of said syringe connection piece.

20. A syringe cylinder in accordance with claim 16, wherein said retaining element includes an internal thread defined by said outer wall for receiving external threads of the cap.

* * * * *